US00PP19708P2

(12) United States Plant Patent
Kako et al.

(10) Patent No.: US PP19,708 P2
(45) Date of Patent: Feb. 10, 2009

(54) ***TORENIA* PLANT NAMED 'SUNRENIPINK'**

(50) Latin Name: ***Torenia* sp.**
Varietal Denomination: Sunrenipink

(75) Inventors: Tetsuya Kako, Shiga (JP); Kiyoshi Miyazaki, Shiga (JP); Kazunari Iwaki, Kanagawa (JP); Takeshi Kanaya, Shiga (JP); Kenichi Suzuki, Osaka (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/079,288

(22) Filed: Mar. 25, 2008

(51) Int. Cl.
*A01H 5/00* (2006.01)

(52) U.S. Cl. ..... Plt./487

(58) Field of Classification Search ..... Plt./487
See application file for complete search history.

*Primary Examiner*—Annette H Para
(74) *Attorney, Agent, or Firm*—C. A. Whealy

(57) ABSTRACT

A new and distinct cultivar of *Torenia* plant named 'Sunrenipink', characterized by its compact and mounding to trailing plant habit; freely branching habit; freely flowering habit; long flowering period; purple-colored flowers; and good garden performance.

1 Drawing Sheet

Botanical designation: *Torenia* sp.
Cultivar denomination: 'Sunrenipink'.

BACKGROUND OF THE INVENTION

The present invention relates to a new and distinct cultivar of *Torenia*, botanically known as *Torenia* sp. and hereinafter referred to by the name 'Sunrenipink'.

The new *Torenia* is a whole plant mutation of a proprietary selection of *Torenia* sp. identified as code number TH1, not patented. The new *Torenia* was discovered and selected by the Inventors as a single plant in a controlled green house environment in Higashiomi, Shiga, Japan in March, 2006.

Asexual reproduction of the new *Torenia* by vegetative cuttings in a controlled environment in Higashiomi, Shiga, Japan since October, 2006, has shown that the unique features of this new *Torenia* are stable and reproduced true to type in successive generations.

SUMMARY OF THE INVENTION

The cultivar Sunrenipink has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunrenipink'. These characteristics in combination distinguish 'Sunrenipink' as a new and distinct cultivar of *Torenia:*

1. Compact and mounding to trailing plant habit.
2. Freely branching habit.
3. Freely flowering habit.
4. Long flowering period.
5. Purple-colored flowers.
6. Good garden performance.

Plants of the new *Torenia* differ primarily from plants of the parent selection in flower color as plants of the parent selection have violet-colored flowers. In addition, plants of the new *Torenia* are smaller than plants of the parent selection.

Plants of the new *Torenia* can also be compared to plants of the cultivar Sunreniririepa, disclosed in a U.S. Plant Pat. No. 14,302. In side-by-side comparisons conducted in Higashiomi, Shiga, Japan, plants of the new *Torenia* and the cultivar Sunreniririepa differed in the following characteristics:

1. Plants of the new *Torenia* were smaller than plants of the cultivar Sunreniririepa.
2. Plants of the new *Torenia* and the cultivar Sunreniririepa differed in flower color as plants of the cultivar Sunreniririepa had red purple-colored flowers.

BRIEF DESCRIPTION OF THE PHOTOGRAPHS

The accompanying colored photographs illustrate the overall appearance of the new *Torenia,* showing the colors as true as it is reasonably possible to obtain in colored reproductions of this type. Colors in the photographs may differ slightly from the color values cited in the detailed botanical description which accurately describe the colors of the new *Torenia.*

The photograph at the top of the sheet comprises a side perspective view of a typical flowering plant of 'Sunrenipink' grown in a container.

The photograph at the bottom of the sheet is a close-up view of a typical flower of 'Sunrenipink'.

DETAILED BOTANICAL DESCRIPTION

The aforementioned photographs and following observations, measurements and values describe plants grown in Higashiomi, Shiga, Japan, under commercial practice during the autumn in a polyethylene-covered greenhouse with day temperatures averaging 20° C. and night temperatures averaging 10° C. Plants had been growing for about five months when the photographs and description were taken. In the following description, color references are made to The Royal Horticultural Society Colour Chart, 2001

Edition, except where general terms of ordinary dictionary significance are used.

Botanical classification: *Torenia* sp. cultivar Sunrenipink.

Parentage: Whole plant mutation of a proprietary selection of *Torenia* sp. identified as code number TH1, not patented.

Propagation:

*Type.*—By vegetative cuttings.

*Time to initiate roots.*—About one week at 20° C. to 25° C.

*Time to produce a rooted young plant roots.*—About three to four weeks at 20° C. to 25° C.

*Root description.*—Fine, fibrous and fleshy; brown in color.

*Rooting habit.*—Freely branching.

Plant description:

*Plant form/habit.*—Compact and mounded to trailing plant habit; outwardly spreading; vigorous growth habit. Freely branching habit; pinching enhances branching; about 17 lateral branches develop per plant.

*Plant height.*—About 20.3 cm.

*Plant width (spread).*—About 50 cm.

*Lateral branches.*—Length: About 20.5 cm. Diameter: About 1.8 mm. Internode length: About 3.6 cm. Aspect: Decumbent. Texture: Smooth, glabrous. Color: Close to N199A.

Foliage description:

*Arrangement.*—Opposite, simple.

*Length.*—About 2.7 cm.

*Width.*—About 1.7 cm.

*Shape.*—Ovate.

*Apex.*—Acute.

*Base.*—Cordate.

*Margin.*—Serrate.

*Texture, upper surface.*—Pubescent.

*Texture, lower surface.*—Smooth, glabrous.

*Venation pattern.*—Pinnate; reticulate.

*Color.*—Developing and fully expanded leaves, upper surface: Close to 137C; venation, close to 144D. Developing and fully expanded leaves, lower surface: Close to 146B; venation, close to 144D.

*Petiole.*—Length: About 6 mm. Diameter: About 1 mm. Texture, upper and lower surfaces: Pubescent. Color, upper and lower surfaces: Close to 148D.

Flower description:

*Flower type/habit.*—Single flowers borne in upper leaf axils; corolla bilabiate and calyx tubular; flowers face obliquely upright. Freely flowering habit with about 62 open flowers per plant.

*Fragrance.*—None detected.

*Natural flowering season.*—Long flowering period; continuously flowering from early summer to late autumn in Japan. Flowers not persistent.

*Postproduction longevity.*—Flowers last about four days on the plant.

*Flower buds.*—Height: About 1.5 cm. Diameter: About 4.2 mm. Shape: Lenticular. Color: N78A.

*Flower diameter.*—About 3.2 cm by 2.6 cm.

*Flower depth.*—About 4 cm.

*Throat diameter.*—About 9.5 mm.

*Tube diameter, base.*—About 2.5 mm.

*Tube length.*—About 2.6 cm.

*Petals.*—Quantity per flower: One upper or banner petal, two lateral petals and one lower petal in a single whorl, fused. Upper petal: Length: About 1.1 cm. Width: About 1.7 cm. Shape: Elliptic. Apex: Mucronate to truncate. Margin: Entire; slightly undulating. Texture, upper and lower surfaces: Smooth, glabrous; velvety. Color: Developing petals, upper surface: Close to N78A; towards the throat, close to N81D. Developing petals, lower surface: Close to N78A. Fully developed petals, upper surface: Close to N78C; towards the throat, close to 84D. Fully developed petals, lower surface: Close to N78C. Lateral petals: Length: About 1.1 cm. Width: About 1.2 cm. Shape: Elliptic. Apex: Mucronate. Margin: Entire. Texture, upper and lower surfaces: Smooth, glabrous; velvety. Color: Developing petals, upper surface: Close to N79C. Developing petals, lower surface: Close to N78A. Fully developed petals, upper and lower surfaces: Close to N78C. Lower petal: Length: About 9.4 mm. Width: About 1.3 cm. Shape: Elliptic. Apex: Rounded. Margin: Entire. Texture, upper and lower surfaces: Smooth, glabrous; velvety. Color: Developing petals, upper surface: Close to N79C; towards the throat, close to N78D. Developing petals, lower surface: Close to N78A. Fully developed petals, upper and lower surfaces: Close to N78C. Throat color: Close to N78C; lines, close to 77A. Tube color: Close to N78A to N78B.

*Sepals.*—Quantity per flower: Typically five fused into two lobes. Calyx length: About 1.6 cm. Calyx diameter: About 5.6 mm. Texture, upper and lower surfaces: Smooth, glabrous. Color, upper and lower surfaces: Close to 145D.

*Peduncles.*—Length: About 1.7 cm. Diameter: About 1.3 mm. Texture: Smooth, glabrous. Color: Close to 144A.

*Reproductive organs.*—Stamens: Quantity per flower: Typically four; two pairs of fused anthers. Filament length: About 4.5 mm to 12 mm. Anther shape: Ellipsoidal. Anther length: About 3.9 mm. Anther color: Close to N77B. Pollen amount: Scarce. Pollen color: Close to 11B. Pistils: Quantity per flower: One. Pistil length: About 2.6 cm. Stigma shape: Elliptic. Stigma color: Close to 77D. Style color: Close to 77D. Ovary color: Close to 138A.

*Seed/fruit.*—Seed and fruit development have not been observed.

Disease/pest resistance: Plants of the new *Torenia* have not been noted to be resistant to pathogens and pests common to *Torenia*.

Garden performance: Plants of the new *Torenia* have been observed to have good garden performance and to tolerate rain, wind and temperatures from about 5° C. to about 30° C.

It is claimed:

1. A new and distinct *Torenia* plant named 'Sunrenipink' as illustrated and described.

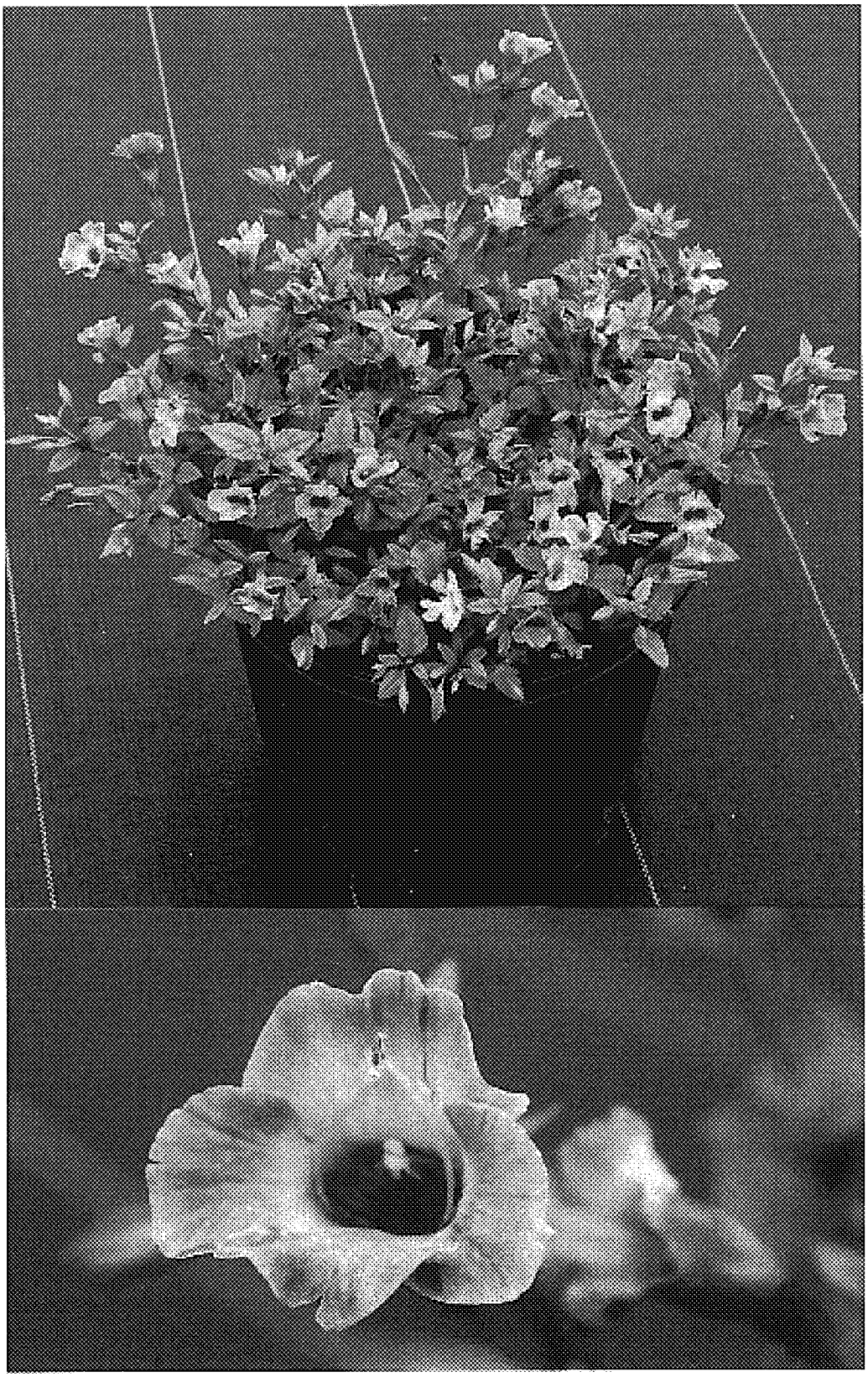

* * * * *